(12) United States Patent
Bormet

(10) Patent No.: US 12,052,526 B2
(45) Date of Patent: *Jul. 30, 2024

(54) IMAGING SYSTEM HAVING STRUCTURAL DATA ENHANCEMENT FOR NON-VISIBLE SPECTRA

(71) Applicant: KARL STORZ Imaging, Inc., Goleta, CA (US)

(72) Inventor: Jonathan Bormet, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,812

(22) Filed: May 12, 2023

(65) Prior Publication Data

US 2023/0283742 A1 Sep. 7, 2023

Related U.S. Application Data

(63) Continuation of application No. 17/484,097, filed on Sep. 24, 2021, now Pat. No. 11,689,689, which is a continuation of application No. 16/712,191, filed on Dec. 12, 2019, now Pat. No. 11,159,749.

(51) Int. Cl.
| | |
|---|---|
| *A61K 35/12* | (2015.01) |
| *A61B 90/00* | (2016.01) |
| *G06K 9/00* | (2022.01) |
| *G06T 7/00* | (2017.01) |
| *H04N 5/33* | (2023.01) |
| *G01N 21/359* | (2014.01) |

(52) U.S. Cl.
CPC ............. *H04N 5/33* (2013.01); *A61B 90/37* (2016.02); *G06T 7/0012* (2013.01); *G01N 21/359* (2013.01)

(58) Field of Classification Search
CPC . G06T 5/50; G06K 9/00; H04N 23/11; A61K 35/12
USPC ........ 382/100, 103, 106–107, 128–132, 162, 382/168, 172–173, 190, 209, 254, 264, 382/286–291, 305, 321; 359/385; 348/95, 164; 600/129, 181; 345/629
See application file for complete search history.

(56) References Cited

U.S. PATENT DOCUMENTS

| | | | | |
|---|---|---|---|---|
| 6,821,245 | B2 * | 11/2004 | Cline | A61B 5/0084 600/181 |
| 8,784,301 | B2 * | 7/2014 | McDowall | H04N 13/243 600/129 |
| 9,675,236 | B2 * | 6/2017 | McDowall | A61B 1/00096 |
| 2013/0044126 | A1 * | 2/2013 | Yamada | G06T 5/50 345/629 |
| 2014/0205150 | A1 * | 7/2014 | Ogawa | G01B 11/14 382/106 |

(Continued)

*Primary Examiner* — Seyed H Azarian
(74) *Attorney, Agent, or Firm* — David N. Villalpando

(57) ABSTRACT

An imaging system includes a light source for emitting visible light and infrared light and a camera head unit configured to capture visible light image data so as to generate a visible light image frame and configured to capture infrared image data so as to generate an infrared image frame. A camera control unit is configured to extract a structural data from the visible light image frame. The camera control unit is further configured to apply the structural data to the infrared image frame so as to enhance the infrared image with structural data.

10 Claims, 7 Drawing Sheets
(3 of 7 Drawing Sheet(s) Filed in Color)

(56) References Cited

U.S. PATENT DOCUMENTS

2018/0024341 A1\* 1/2018 Romanowski ......... G02B 21/06
  359/385

\* cited by examiner

IMAGING SYSTEM HAVING STRUCTURAL DATA ENHANCEMENT FOR NON-VISIBLE SPECTRA

CROSS REFERENCE TO RELATED APPLICATIONS

This application is a continuation of U.S. application Ser. No. 17/484,097 filed on Sep. 24, 2021, and entitled, "Infrared Imaging System Having Structural Data Enhancement," which is in turn a continuation of U.S. application Ser. No. 16/712,191 filed on Dec. 12, 2019, titled "Infrared Imaging System Having Structural Data Enhancement," and issued as U.S. Pat. No. 11,159,749 on Oct. 26, 2021; the entire contents all above named applications are incorporated herein by reference.

TECHNICAL FIELD

The disclosure relates to an imaging system for medical procedures.

BACKGROUND

Surgical imaging systems may include one or more light sources that emit both visible light and non-visible light such as infrared light. The visible light is typically used as a reference light or illuminating light, while the infrared light is typically used as an excitation light that excites a dye to emit light through fluorescence in the infrared spectrum. Visible light provides the surgeon with an image as seen by the human eye, whereas the image generated by the fluorescence light provides an infrared image of tissue characteristics such as blood flow, inflammation and the like. A depiction of a visible light image ("VL image") and a non-visible light image, such as the infrared image ("IR image"), is illustratively shown in FIGS. 1A and 1B, respectively.

It should be appreciated that the VL image provides a clearer view of structural features of a surgical site such as veins, different body tissue and the like whereas the IR image provides a visual depiction of aspects such as blood flow within the tissue and/or diseased tissue. FIG. 1B depicts how the IR image lacks the structural details shown in the VL image. Thus, the two images are analyzed by the surgeon during a medical procedure. In some cases, the IR image is colored and then combined with the VL image. For example, data processing hardware is configured to use a color map, such as a look-up table (LUT), to generate a pseudo-color mapped image (colored IR image) based on the IR image which is then combined with the VL image to create a combined image. This provides the surgeon the benefit of viewing the structural details in context with tissue conditions such as blood flow or disease. However, the colored IR image obscures some of the structural detail provided in the VL image when combined, as shown in the combined image of FIG. 2.

SUMMARY

Accordingly, it is desirable to enhance the IR image or colored IR image to includes structural data so as to facilitate improved real time analysis of the surgical site.

One aspect of the disclosure provides an imaging system generating an IR image enhanced with structural data. The system includes a light source for emitting infrared light and visible light. A camera head unit captures VL image data so as to generate VL image frame and captures the IR image data so as to generate an IR image frame.

The imaging system also includes a camera control unit ("CCU") configured to execute instructions for executing imaging functions. The CCU is configured to extract a structural data from the VL image frame. The CCU is further configured to apply the structural data to the IR image frames so as to enhance the infrared light video with the extracted structural data so as to generate an enhanced IR image frame.

Implementations of the disclosure may include one or more of the following optional features. In some implementations, the structural data is an edge identified in the VL image frame. The edge may be identified using known image filters which detect a contrast in the VL image frame. Such image filters illustratively include a bilateral filter, a high-pass and/or a low-pass filter.

In some implementations, the CCU is further configured to detect the structural data by converting the VL image frames into grayscale image frames prior to extracting the structural data.

In some implementations, the CCU scales the structural data by a predetermined factor so as to generate an enhancement signal. The enhancement signal is then applied to the IR image frame. Thus, the enhancement of the structural data shown in the enhanced IR image may be increased or decreased based upon the enhancement signal.

In some implementations, the data processing hardware is configured to generate a color map of the IR image data. The color map depicts various intensities of a color based upon the diffusion of the dye within the tissue. The CCU is further configured to apply the structural data to the color map.

In some implementations, the structural data is determined by processing a predetermined luminance identified in the VL image frame. This may be done in conjunction with or in lieu of processing a contrast in the VL image frame.

A method for generating an IR image enhanced with structural data is also provided. The method may be implemented in an imaging system having one or more light sources that emit both white (i.e., visible) light and infrared light and a first image sensor and a second image sensor are configured to capture the visible light and the infrared light respectively.

The method includes the step of obtaining a VL image frame and obtaining an IR image frame. The method includes the steps of extracting a structural data from the VL image frame and applying the structural data to the IR image frame so as to generate an enhanced IR image frame. Accordingly, the enhanced IR image frame includes structural data extracted from the VL image frame.

Implementations of the method disclosed herein may include one or more of the following optional features. In some implementations, the structural data is an edge identified in the VL image frame, wherein the edge may be identified by a contrast in the VL image. The contrast may be determined using known filters, such as a bilateral filter, a high-pass and/or low-pass filter.

In some implementations, the method further includes the step of converting the VL image frames into grayscale image frames prior to extracting the structural data.

In some implementations, the structural data is scaled by a predetermined factor so as to generate an enhancement signal. Thus, the enhancement of the structural data shown in the enhanced IR image may be increased or decreased based upon the enhancement signal.

In some implementations, the method includes the step of generating a color map of the IR image data and applying the structural data to the IR image frame.

In some implementations, the structural data is determined by processing a predetermined luminance identified in the VL image frame.

The details of one or more implementations of the disclosure are set forth in the accompanying drawings and the description below. Other aspects, features, and advantages will be apparent from the description and drawings, and from the claims.

BRIEF DESCRIPTION OF THE DRAWINGS

The embodiments set forth in the drawings are illustrative and exemplary in nature and not intended to limit the subject matter defined by the claims. The patent or application file contains at least one drawing executed in color. Copies of this patent or patent application publication with color drawing(s) will be provided by the Office upon request and payment of the necessary fee. The following description of the illustrative embodiments can be understood when read in conjunction with the following drawings, where like structure is indicated with like reference numerals and in which:

DETAILED DESCRIPTION OF PREFERRED EMBODIMENTS

Implementations herein are directed toward an imaging system configured to generate an IR image enhanced with structural data. In one aspect, the imagining system generates a VL image and extracts structural data from the VL image. The structural data is then applied to the IR image so as to generate an enhanced IR image which provides clear visual context of anatomical features. As used herein, the term "applied" refers to the technique of overlaying one image frame with another, wherein anatomical features from one image frame are aligned with anatomical features of the other image frame.

For illustrative purposes, the imaging system is described herein within the context of endoscopy. Endoscopy, a non-surgical medical procedure used to examine internal body cavities (e.g., a digestive tract), is increasingly used as an effective diagnostic tool. The procedures are typically performed using endoscopes, which include, in their most basic form, a flexible tube with a light source configured to emit visible light and infrared light. A CCU controls the exposure of a pair of image sensors configured to detect light in the visible spectrum and infrared spectrum respectively. The flexible tube is passed through an orifice (e.g., the mouth) of a patient and the camera records images illuminated by the light source.

Figure 1A:
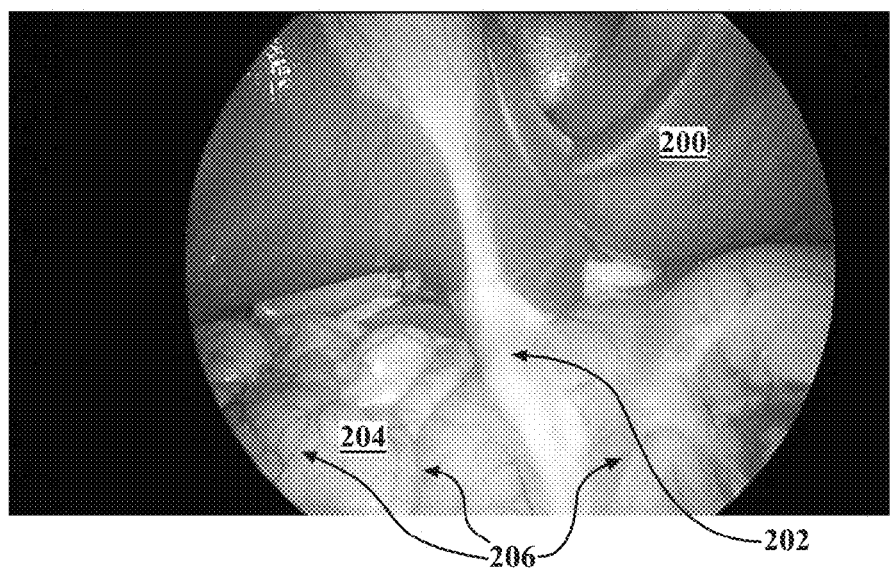
FIG. 1A is a view of a VL image frame shown in color.

FIG. 1A is an illustrative view of a VL image frame 100 taken from a laparoscopic procedure. The liver 200, bile duct 202 and the intestine 204 are clearly distinguishable, as are the veins. For illustrative purposes, an example of the imaging system will be made in the context of a laparoscopic procedure.

In some procedures, non-visible imaging may also be used. For example, infrared light is used to provide fluorescent imaging. For instance, indocyanine green ("ICG") is a cyanine dye used frequently in medical diagnostics and endoscopy for determining cardiac output, hepatic function, liver and gastric blood flow, and for ophthalmic angiography. For example, ICG distribution within the tissue enables intraoperative evaluation of a tissue perfusion and vacuolization, identification of critical neurovascular structures and differentiation of tissue plains between lesions and adjacent structures. ICG, when irradiated with infrared light (750 nm and 950 nm), emits light through fluorescence. When viewed using an image sensor, the fluorescence generates an IR image in the infrared spectrum. The IR image may be output by the sensor as a monochromatic IR image which obscures some of the structural definition of the body, as shown in FIG. 1B when compared to FIG. 1A.

Figure 1B:
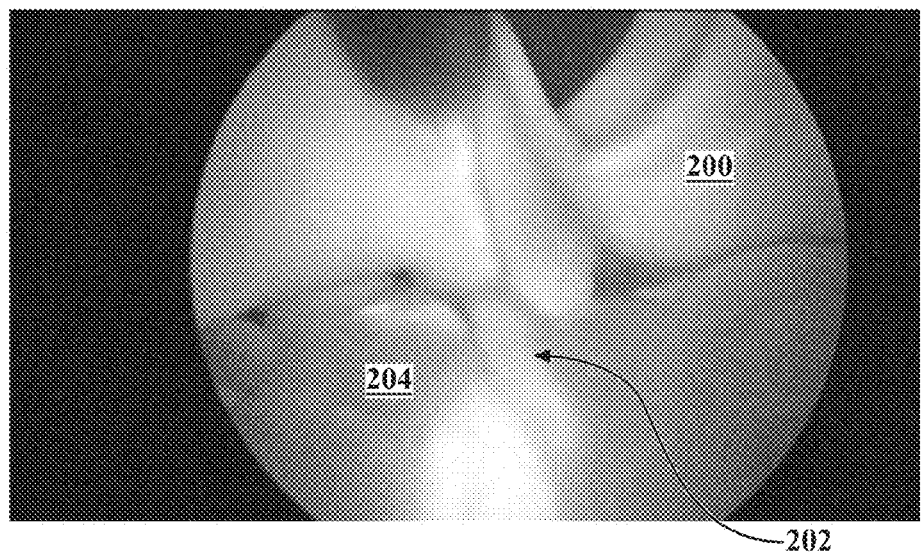
FIG. 1B is a view of an IR image frame shown in color.
Figure 2:
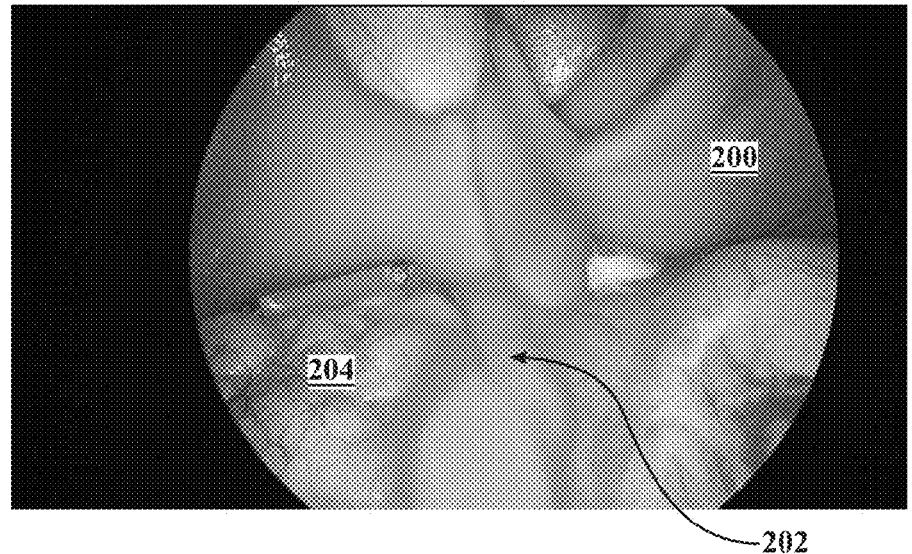
FIG. 2 a view of a combined image frame combining the VL image frame shown in FIG. 1A with a colored IR image frame based on the IR image frame shown in FIG. 1B, shown in color.

In FIG. 1B, the intensity of the image correlates to the diffusion of the dye. Thus, the intensity of the dye collected in the liver 200 and passing through the bile duct 202 is more intense relative to the intestine 204. FIG. 1B also depicts how structural data such as the edges defining the liver 200 from the bile duct 202 and the intestines 204 are not as clear as what is shown in FIG. 1A. Other structural data in the IR image, such as the veins 206 are also obscured by the irradiating dye. With reference now to FIG. 2, the IR image may be colored using a color map to generate a colored IR image and then combined with the visible light image shown in FIG. 1A to create a combined image. FIG. 2 illustrates how the color IR image obscures some of the details of the visible light image when combined. In particular, some of the edges of the liver 200, bile duct 202, and intestines 204 near the colored IR image are shown as being generally blurry, and details such as the veins 206 are hidden.

Figure 3:
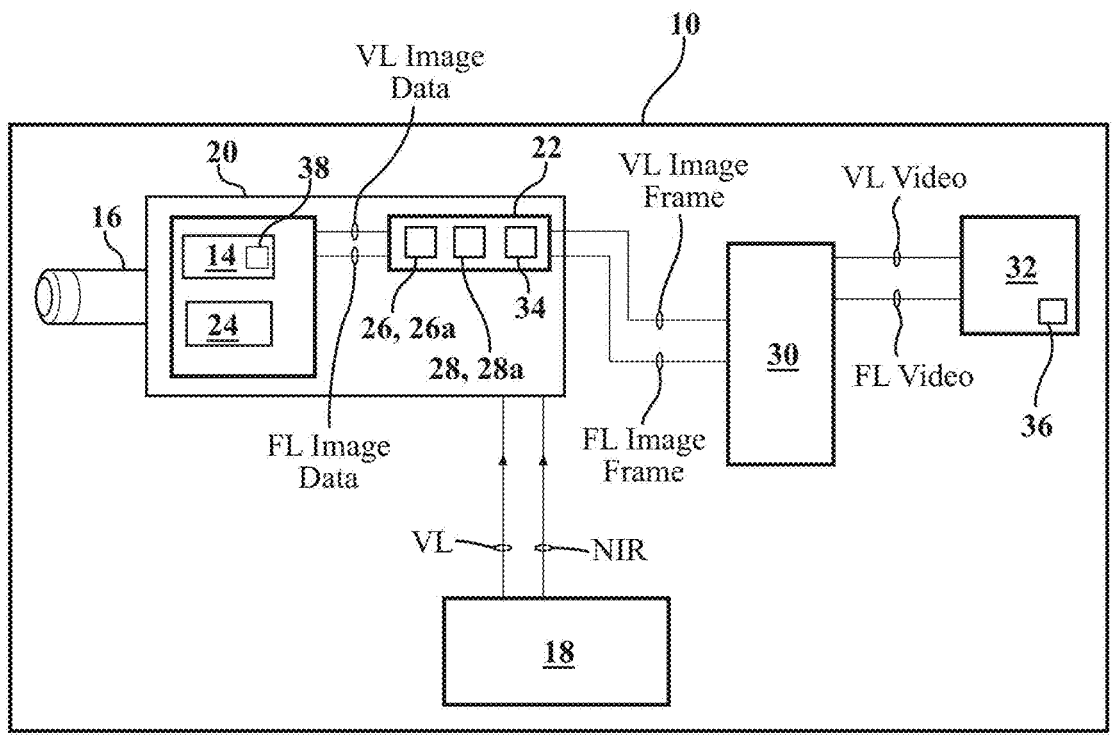
FIG. 3 is a schematic view of an imaging system according to one or more embodiments described herein.

With reference now to FIG. 3, an imaging system 10, according to one aspect, that generates an enhanced IR image frame enhanced with structural data 12 (illustratively shown in FIG. 5 as depicted in a grayscale frame 36) is provided. For illustrative purposes, a description of the imaging system 10 is provided within the context of an endoscopic system. However, it should be appreciated that the imaging system 10 may be utilized in other applications, illustratively including an exoscope, borescope and other systems having two or more illumination-types and one or more image sensors 14. Furthermore, although the imaging system 10 is described with respect to medical applications using fluorescing dye, it should be understood that industrial applications using other combinations of visible light and infrared light of narrow wavelength ranges may benefit from the same principles.

The imaging system 10 includes an endoscope 16, one or more light sources 18, a camera head 20 and a CCU 22. In some examples, the light source 18 is included within the camera head 20. In other examples, the endoscope 16 and the camera head 20 may form an integral unit known in the art as a videoscope. FIG. 3 provides an example where the camera head 20 and the CCU 22 are formed as an integral unit, but it should be appreciated that the CCU 22 may be a separate unit in communication with the camera head 20. Regardless of the specific configuration, the principles of the present disclosure apply to various examples of video imaging systems 10 as previously noted. The camera head 20, light source 18 and CCU 22 are coupled to each other wirelessly or through a wired connection.

The light source 18 emits both visible light (VL) and near infrared light (NIR). In some examples, a timer 24 is provided to control the operation of the light source 18 so as to switch between emitting VL and NIR light and the light source 18 is coupled to the endoscope 16 so as to illuminate the surgical site. The light source 18 may include one or more light-emitting diodes (LEDs) or any other appropriate light-emitting device. Separate light sources 18 may emit the VL and the NIR light respectively. In other examples, both VL and NIR may be simultaneously provided.

Light emitted by the light source 18 travels along a light guide (e.g., an optical fiber) and, after exiting the light guide, illuminates or irradiates a target area of the surgical site (e.g., an internal cavity of a patient). Reflected VL (i.e., VL that has reflected from the target area) and emitted fluorescent light (i.e., light emitted by, for example, ICG that has been irradiated by NIR light) are directed back through the optical pathway and are captured by the camera head 20 and processed as image data, VL image data and IR image data respectively. In particular, the image sensors 14 are controlled by the CCU 22 so as to be exposed during the emission of respective VL and IR light.

The image sensors 14 may be a complementary metal oxide semiconductor (CMOS) or a Charged Coupled Device (CCD). It should be appreciated that any pixelated image sensor 14 currently known or later developed may be modified and adopted for use herein. The image sensors 14, in some implementations, include color filter arrays (CFAs).

The image sensors 14 transmit VL image data and IR image data to the CCU 22. The CCU 22 is configured to execute instructions for performing imaging functions. For example, the CCU 22 may include computing resources 26 (e.g., data processing hardware 26a, field programmable gate array ("FPGA") and the like) for executing instructions configured to perform image processing and storage resources 28 (e.g., memory hardware 28a). The CCU 22 processes the VL image data and the IR image data to produce a respective VL image frame 100 and an IR image frame 102, as illustratively shown in FIG. 1A and FIG. 1B respectively. The IR image frame 102 may be converted to a color mapped image frame ("colored IR image frame") as shown in FIG. 8B, wherein the colored IR image frame is then superimposed on the VL image as shown in FIG. 2. In some implementations, a display control unit 30 is further configured to compile the VL image frames and the colored IR image frames so as to generate respective VL and IR videos which may be displayed on a display unit 32.

In some implementations, the CCU 22 is disposed physically within the camera head 20 and in wired communication with the image sensors 14. In other implementations, the CCU 22 is in wireless communication with the image sensors 14 (e.g., via wireless, Bluetooth, etc.) and may be remote from the image sensors 14 and/or system. In this case, the CCU 22 may correspond to any appropriate computing device, such as a desktop workstation, laptop workstation, or mobile device (e.g., smart phone or tablet). In yet other implementations, the data may be stored in nonvolatile storage at the system (e.g., a thumb drive) and later removed to be processed at data processing hardware 26a and storage resource 28 such as memory hardware 30a remote from the image sensors 14. The memory hardware 30a stores instructions that when executed on the data processing hardware 26a cause the data processing hardware 26a to execute camera and imaging functions.

Figure 4:
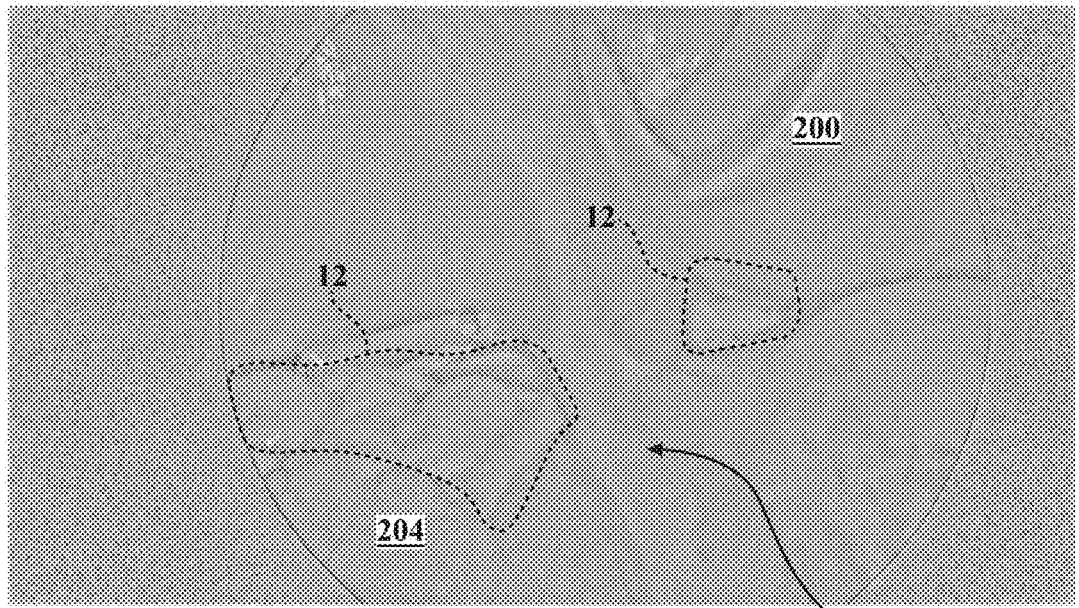
FIG. 4 is a view of a structural data image frame showing the structural data taken from the VL image frame shown in FIG. 1A.
Figure 5:
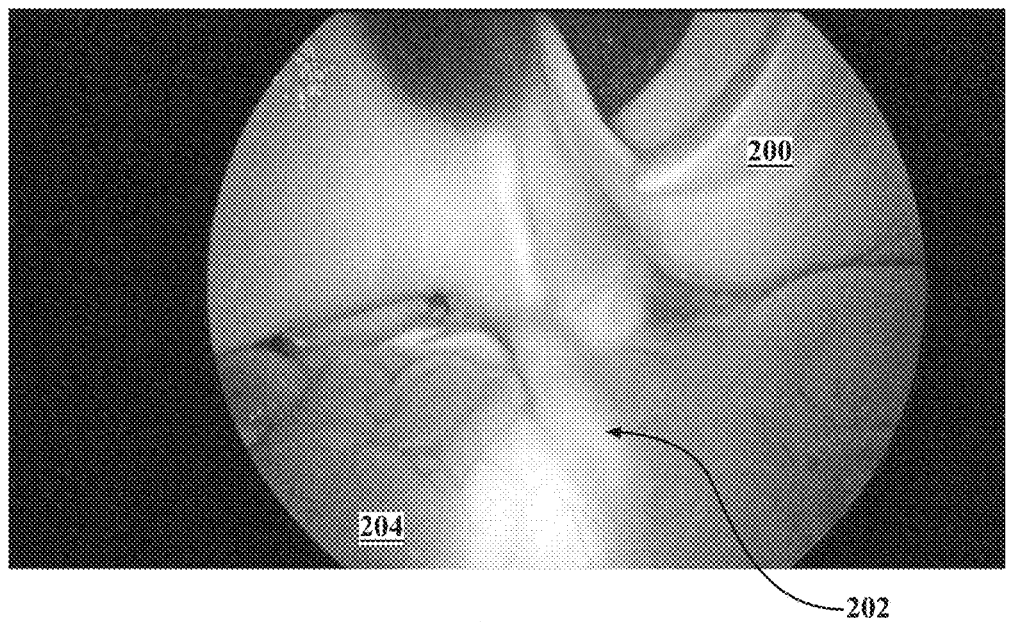
FIG. 5 is a view of an enhanced IR image frame based on the IR image frame shown in FIG. 1B enhanced with the structural data image frame shown in FIG. 4 shown in color.

The CCU 22 processes (i.e., using instructions stored on the storage resources or written on an FPGA) the VL image frame 100 so as to extract structural data 12 (illustratively shown in FIG. 4 in areas surrounded by dotted lines) and apply the structural data 12 to the IR image frame 102 to create an enhanced IR image frame as shown in FIG. 5. In some implementations, the structural data 12 are edges identified in the VL image frame. It should be appreciated that the VL and IR image frames 100, 102 capture substantially the same target area, as shown in FIGS. 1A and 1B.

FIG. 1A depicts a VL image frame, wherein the edges identified by the CCU 22 define the shape of the body tissue and clearly delineates the different tissue and body parts from each other. For example, the edges define the veins 206, liver 200, bile duct 202 and the intestine 204 of the target area.

With reference again to FIG. 4, a depiction of the structural data 12 taken from the VL image frame 100 shown in FIG. 1A is provided. The CCU 22 executes instructions, vis-a-vis a data processing hardware 26a or an FPGA, to extract the structural data 12 from the VL image frame 100. FIG. 4 illustratively shows lines defining the edges of the liver 200, bile duct 202 and the intestine 204, as well as the veins 206.

In one aspect, the edges may be identified using known image filters 34 which may be written as a set of instructions stored in the memory hardware 30a or FPGA. The image filters 34 may be formed as part of the CCU 22. The image filters 34 may be configured to detect a contrast level in the VL image frame 100. Such image filters 34 illustratively include a bilateral filter, a high-pass and/or a low-pass filter which processes the VL image frame 100 so as to produce the structural data 12 illustratively shown in FIG. 4.

Figure 6:
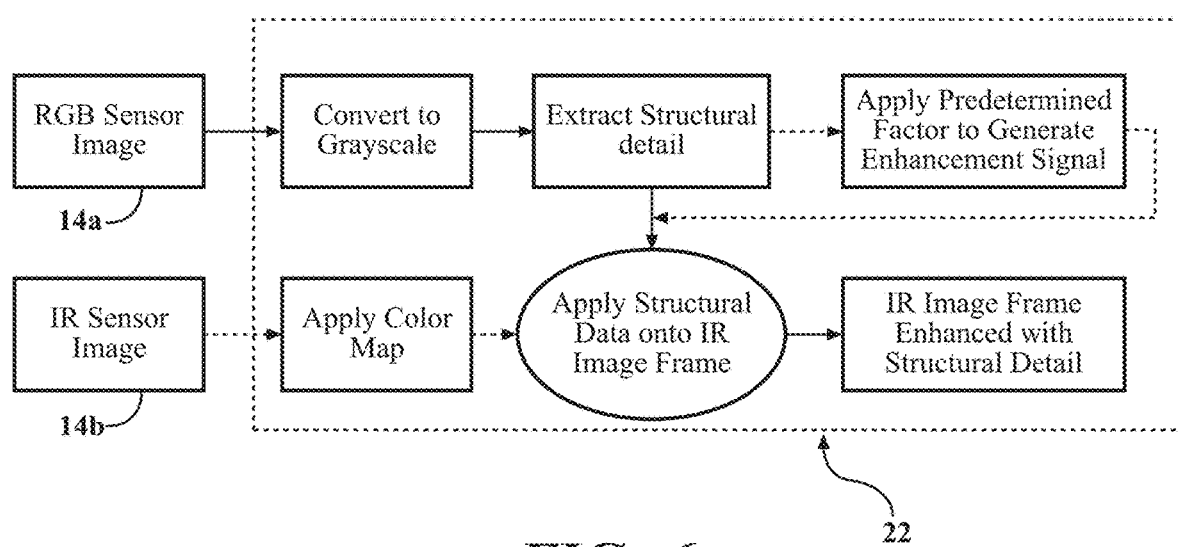
FIG. 6 is a schematic view of a CCU according to one or more embodiments described herein.

Referring now to FIG. 6, in one aspect, the CCU 22 converts the VL image frame 100 into a grayscale image frame 36 as depicted in FIG. 4. Any such an image processing function currently known or later developed to convert a VL image frame 100 into grayscale image frame 36 may be adapted for use herein. For use herein, the term "grayscale image frame" means an image frame which has been processed such that the value of each pixel is a single sample representing only an amount of light, that is, it carries only intensity information so as to only include shades of gray. Thus, the colors (red, green and blue for instance) are removed from the VL image frame 100 and the image is depicted in terms of the intensity of gray. The CCU 22 extracts the structural data 12 from the grayscale image frame 36 and applies the structural data 12 to the IR image frame (such as the one shown in FIG. 1B), so as to generate an enhanced IR image frame enhanced with structural detail as shown in FIG. 5. One benefit of extracting the structural data 12 from a grayscale image frame 36 is that the edges are more easily detected. This is clearly shown when comparing FIG. 5 with FIG. 1B. In particular, the veins, liver, bile duct and intestine shown in FIG. 5 are more distinct relative to the same part shown in FIG. 1B.

FIG. 6 provides a schematic view of the CCU 22 showing the process for generating an IR image frame enhanced with structural details. The VL image sensors 14*a* and the IR image sensors 14*b* are shown as generating a respective VL image frame 100 and an IR image frame 102, such as VL and IR image frames 100, 102 illustratively shown in FIGS. 1A and 1B respectively. The VL image frame 100 is generated using a color image filter 38, such a Bayer filter to generate a VL image frame 100 have colors in three color channels-Red, Green and Blue ("RGB"). The CCU 22 converts the VL image frame 100 into a grayscale image frame 36. An edge-preserving low pass filter 34, such as a bilateral filter, separates the structural data 12 from the grayscale image frame 36, which may be executed by a FPGA so as to extract the structural data 12, illustratively shown in FIG. 4. As described above, the CCU 22 applies the structural data 12 onto the IR image frame, as shown in FIG. 5.

In some implementations, the grayscale image frame 36 is generated by processing a luminance information of the VL image frame 100. The luminance information may be taken from an average of the three color channels ("RGB") of the VL image frame 100, or a single color, e.g. red, blue or green. The luminance information as is known in the art is an intensity of the VL image data for each pixel. In such a manner, it is possible for determining structural data 12 using luminance information.

As stated above, the grayscale image frame 36 may be generated by a single color, wherein the VL image frame 100 is processed such that the value of each pixel is a single sample representing only an amount of light. That is, the value of each pixel carries only intensity information so as to only include a shade of a single color, such as red, green or blue. The CCU 22 processes the image data from the single colored image frame so as to generate a grayscale image frame 36. It should be appreciated that any process known or later developed to generate a grayscale image frame 36 may be adapted for use herein.

Figure 7A:
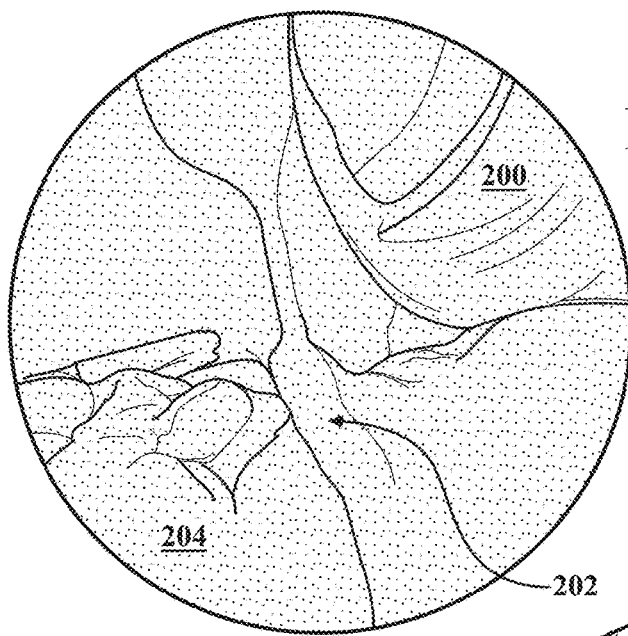
FIG. 7A is an illustrative view of structural data in a grayscale image frame.
Figure 7B:
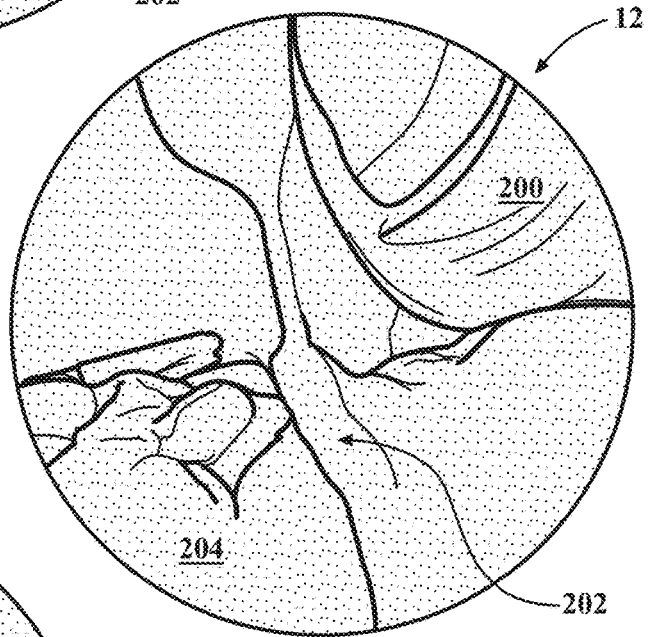
FIG. 7B is a view of the structural data further enhanced to increase definition of some structural data relative to FIG. 7A.
Figure 7C:
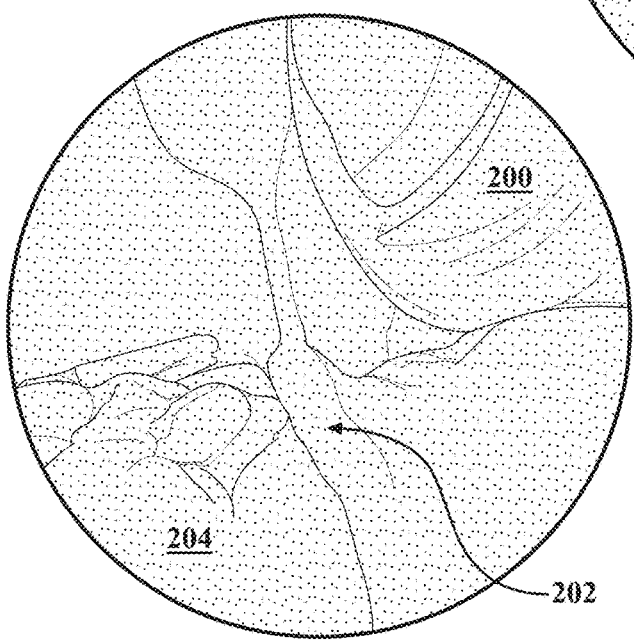
FIG. 7C is a view of the structural data further enhanced to decrease definition of some structural data relative to FIG. 7A.

With reference again to now to FIGS. 7A-7C, another aspect of the imaging system 10 is provided. In such an aspect, the CCU 22 adjusts the enhancement of the structural data 12 by a predetermined factor by applying an enhancement signal. FIG. 7A shows the grayscale image frame 36 wherein the structural data 12 is not further enhanced. FIG. 7B shows an example where enhancement of the structural data 12 is increased or emphasized, for example by increasing the edge widths or intensities by a factor greater than 1, and thus the edges are sharper and darker relative to the edges shown in FIG. 7A. FIG. 7C shows an example where enhancement of the structural data 12 is decreased or deemphasized, for example by decreasing the edge widths or intensities by a factor lesser than one (1) but greater than zero (0), and thus the edges are thinner and dimmer relative to the edges shown in FIGS. 7A and 7B. It should be appreciated that the enhancement of the structural data 12 is depicted by an increase or decrease in the thickness for illustrative purposes, and that the scaled structural data 12 may be displayed in terms of an increase or decrease in intensity.

The predetermined factor may be adjusted using an input 40 such as a dial, a keyboard, touchscreen voice command or the like. Thus, the enhancement of the structural data 12 shown in the enhanced IR image of FIG. 5 may be increased or decreased based upon the enhancement signal. The input may be actuated in real time, adjusting the predetermined factor so as to adjust the enhancement signal in real time. As such, the enhancement of the structural data 12 may be adjusted based upon the intensity of the fluorescence in the IR image frame. For instance, should the intensity of the fluorescence in the IR image frame obscure the structural data 12, the enhancement signal may be increased by the input so as to better delineate the different tissues within the surgical site, e.g. distinguish the liver from the bile duct and the intestines.

Figure 8A:
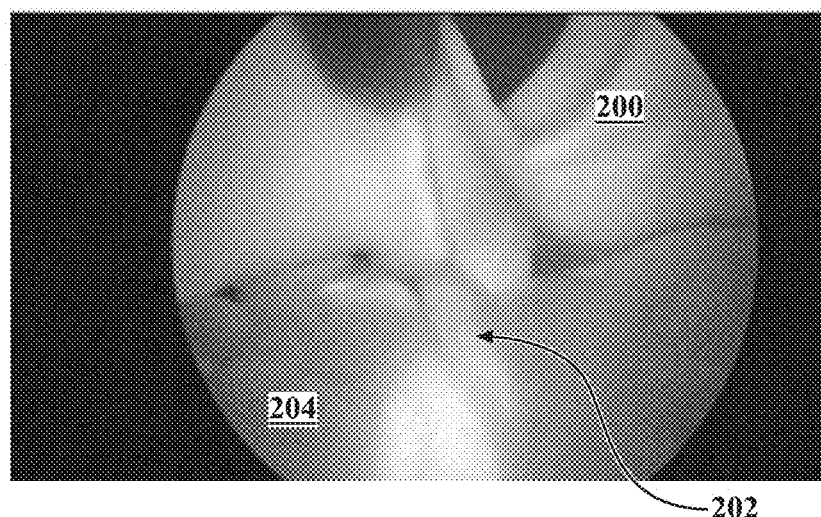
FIG. 8A is a view of an IR image frame shown in color.
Figure 8B:
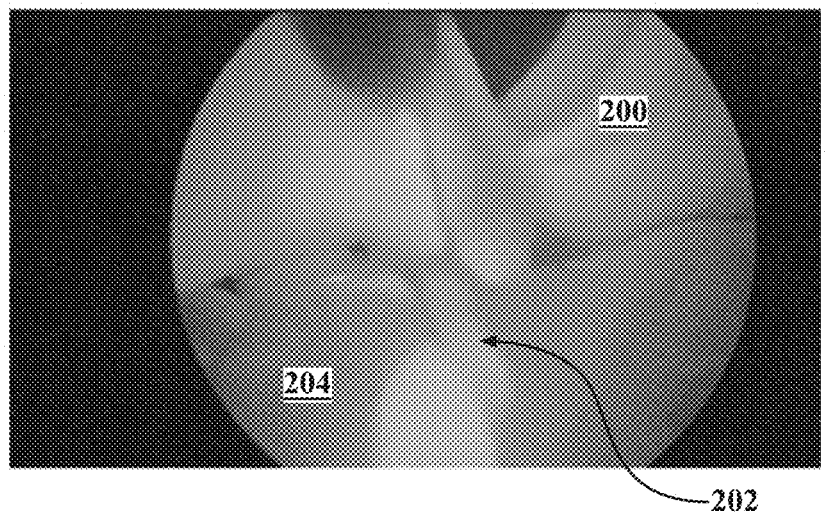
FIG. 8B is a view of a colored IR image frame based on the IR image frame shown in FIG. 8B with a color map applied shown in color.
Figure 8C:
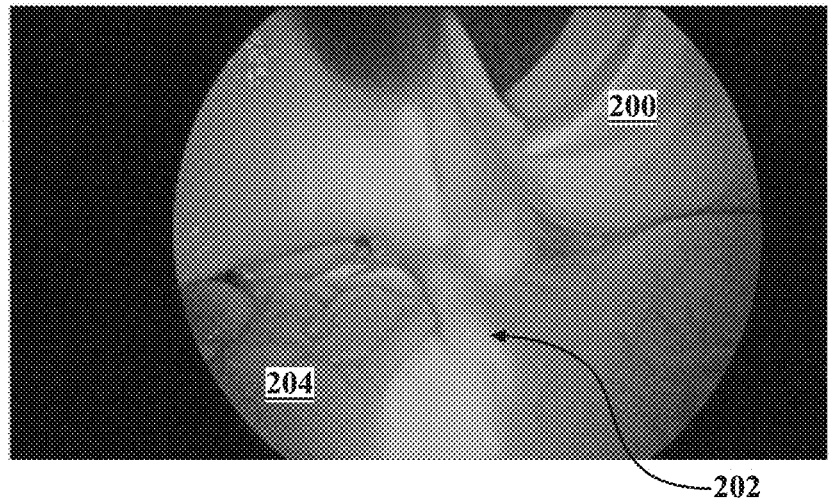
FIG. 8C is a view of an enhanced colored IR image frame based on the colored IR image frame shown in FIG. 8B with structural data extracted from a VL image shown in color.

With reference now to FIGS. 8A-8C, an aspect of the imaging system 10 is described wherein the IR image frame is colored. In such an aspect, the CCU 22 is configured to generate colored IR image frame using a color map applied to the IR image data, the color map having a plurality of color planes, any such an image processing function currently known or later developed to generate a colored IR frame may be adapted for use herein. FIG. 8A shows the surgical site of an IR image frame as processed by the CCU 22. FIG. 8B shows the colored IR image frame having a color map applied which is generated by the CCU 22. For illustrative purposes, the color map is shown as being various shades of green; however, it should be appreciated that other colors may be used including multiple colors. FIG. 8B illustrates how the colored IR image further obscures the details of the surgical site, relative to the IR image shown in FIG. 8A. Thus, the delineation of the bile duct 202 and the liver 200, for example is unclear. The CCU 22 is configured to apply the structural data 12 to the colored IR image, as shown in FIG. 8C. FIG. 8C shows the edges of the liver 200, bile duct 202 and intestines 204 are more distinct relative to FIGS. 8A and 8B. FIG. 8C further shows the vein 206, which are obscured in FIGS. 8A and 8B.

Figure 9A:
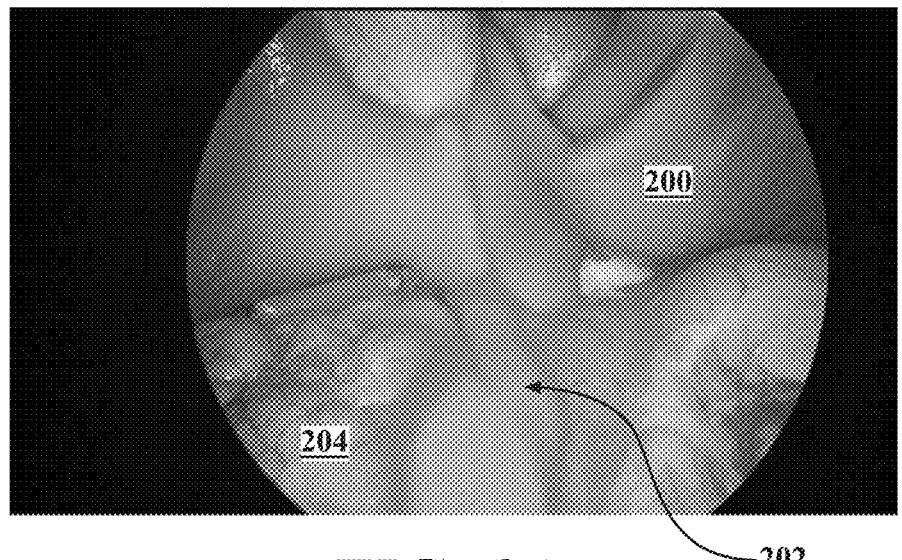
FIG. 9A is a view of a combined image frame based on a VL image frame combined with a colored IR image frame shown in color.
Figure 9B:
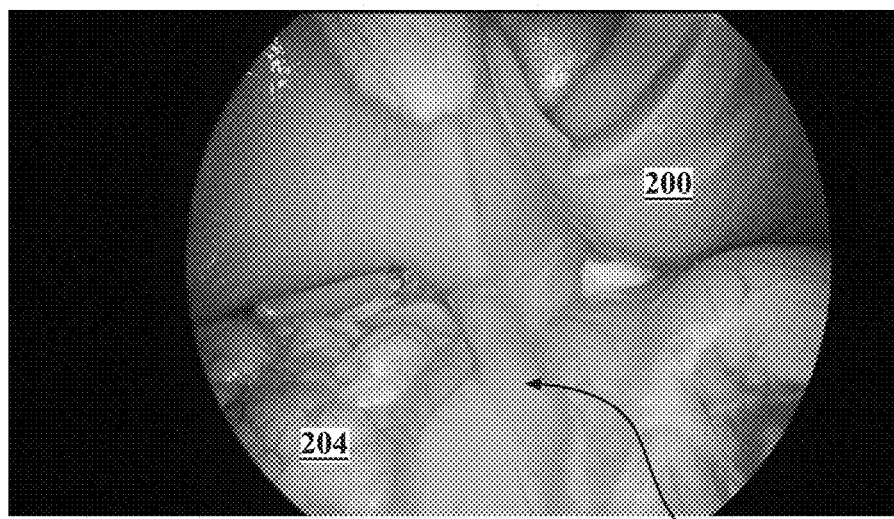
FIG. 9B is a view of an enhanced combined image frame based on the combined image frame shown in FIG. 9A enhanced with structural data applied to the colored IR image frame shown in color.

With reference now to FIGS. 9A and 9B another aspect of the imaging system 10 is provided, wherein a combined image frame is generated by applying the colored IR image onto the VL image. In particular, colored IR image frame 102 has been processed by application of a color map as described above. The structural data 12 is extracted from the VL image frame 100 as described above. For instance, the CCU 22 may process the VL image frame 100 so as to generate a grayscale image frame 36 as shown in FIG. 4, wherein the structural data 12 is extracted and then applied to the colored IR image to generate an enhanced colored IR image frame. The enhanced colored IR image frame is then combined with the VL image frame 100 so as to form an enhanced combined image frame that is enhanced with structural details as shown in FIG. 9B. Preferably, the CCU 22 performs cropping or filtering features to remove any structural data 12 from being applied to the VL image portion of the overlaid image frame. A comparison of FIGS. 9B and 9A shows the advantage of applying the structural data 12 to the color map. In particular, FIG. 9A illustrates how the edges delineating the liver 200 from the bile duct 202 and the intestine 204 are obscured by the color map. However, the structural data 12 of the liver 200, bile duct 202 and the intestines 204 are more visible in FIG. 9B relative to FIG. 9A as the edges extracted from the VL image frame 100 are applied to the colored IR frame portions of the enhanced combined image frame.

The structural data 12 may be extracted from the VL image frames 100 using any of the techniques described above, that is the structural data 12 may be an edge detected by filters, conversion of the VL image frames 100 into grayscale, and luminance information by processing an average of all the colors or a single colored VL image frame 100. The extracted structural data 12 may be adjusted by a predetermined factor which may be adjusted by an input so as to increase, decrease or remove the structural data 12 applied to the colored IR image frames 102, illustratively shown in FIG. 8C.

In another aspect, the camera head 20 is configured to capture VL image data so as to generate at least two VL image frames 100 and configured to capture IR image data so as to generate at least two IR image frames 102. The CCU 22 is configured to compile the VL image frames so as to produce a visible light video and compile the colored IR image frames so as to produce colored IR video. The CCU 22 is further configured to apply the structural data 12 to the IR image frames so as to enhance the colored IR video. The CCU 22 may combine VL light frames 100 and enhanced colored IR frames to generate enhanced combined video. Thus, the imaging system 10 provides a video of the surgical site in both VL and infrared light, wherein frames based on the infrared light (whether IR image frames or colored IR image frames) are enhanced with structural data 12 taken from the VL image frames.

Figure 10:
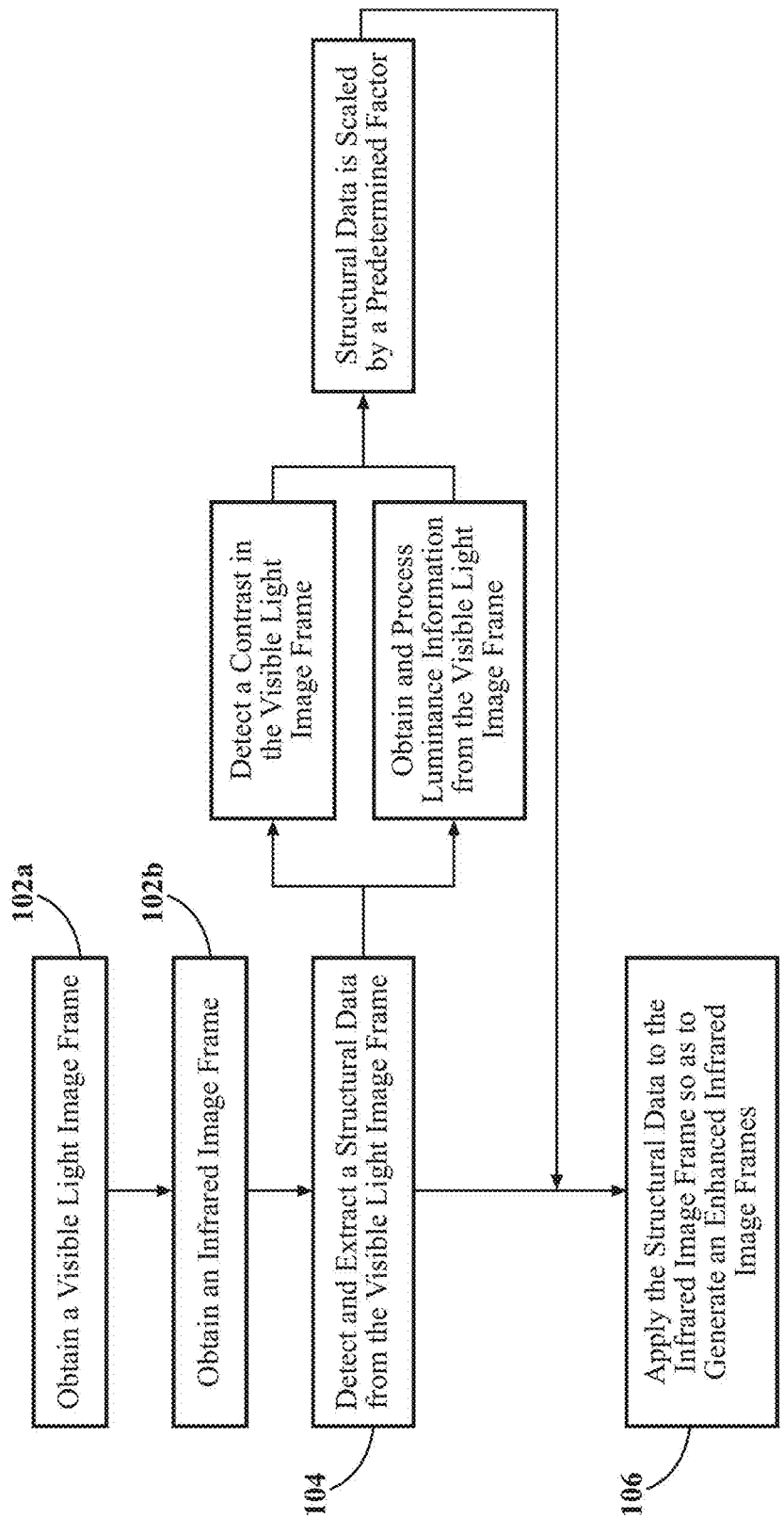
FIG. 10 is a flow chart showing a method of generating an IR image enhanced with structural data.

With reference now to FIG. 10, a method 300 for generating an IR image frame enhanced with structural data 12 is also provided. The method 300 may be implemented in the imaging system 10 described herein, wherein the imaging system 10 includes one or more light sources 18 that emit both white (i.e., visible) light and infrared light. A camera head 20 having a first image sensor 14a and a second image sensor 14b are configured to capture the visible light and the infrared light respectively.

The method 300 includes the steps 302a, 302b of obtaining a VL image frame 100 and obtaining an IR image frame 102. The VL image frame 100 and the IR image frame 102 may be generated by the CCU 22. The method 300 includes the step 304 of detecting and extracting structural data 12 from the VL image frame 100. The method 300 includes the step 306 of applying the structural data 12 onto the IR image frame 102 by the CCU 22 to generate an enhanced IR image frame. As described above, this may be done using a FPGA and/or a data processing hardware 26a. Accordingly, the enhanced IR image frame 102 includes structural data 12 extracted from the VL image frame 100.

The structural data 12 may be an edge identified in VL image frame 100, wherein the edge may be identified by detecting a contrast in the VL image, as shown in step 304a. The contrast may be detected using known filters, such as a bilateral filter, high-pass or low-pass filter. The extracted structural data 12 is converted into a structural data image frame 12a.

In some implementations, the step of extracting the structural data 12 includes converting the VL image frames 100 into grayscale image frames 36 prior to extracting the structural data 12. In some implementations, the step of extracting the structural data 12 includes obtaining luminance information from the VL image frame 100, as shown in step 304b. The luminance information may be taken from an average of the three color channels ("RGB") of the VL image frame 100. Alternatively, the luminance information is taken from a single color. In such an aspect, the VL image frame 100 is processed to remove all but one color.

In some implementations, the structural data 12 is scaled by a predetermined factor so as to generate an enhancement signal, as shown in step 308. Thus, the enhancement of the structural data 12 shown in the enhanced IR image frame 102 may be increased or decreased based upon the enhancement signal. As described above, the predetermined factor may be adjusted manually so as to increase or decrease the visibility of the structural data 12 on the IR image frame 102.

In some implementations, the method 300 includes the step of generating a color map of the IR image data, the color map having a plurality of color planes and the data processing hardware 26a is configured to apply the structural data 12 to the IR image frame 102, as shown in FIG. 8C.

In some implementations, the method 300 includes the step of generating a combined image frame having the colored IR image frame combined with the VL image. In such a step, the colored IR image frame has been processed by application of a color map to the IR image frame. The structural data 12 is extracted from the VL image frame 100 and applied onto the colored IR image frame and combined with the VL image frame 100 so as to generate the enhanced combined image frame.

The method 300 may include the step of cropping or filtering features to remove or prevent any structural data 12 from being applied to VL image portions of the combined image frame. Such a step may help the VL image retain a depiction of the surgical site as seen by the human eye.

The method 300 may further include the step of obtaining at least two VL image frames 100 and at least two IR image frames 102. The CCU 22 is configured to compile the VL image frames 100 so as to produce a visible light video and compile the IR image frames 102 so as to produce an infrared light video, the structural data 12, the CCU 22 is further configured to apply the structural data 12 to the IR image frames so as to enhance the colored light video. Thus, the method 300 provides a video image of the surgical site in both VL and infrared light, wherein the infrared light is enhanced with structural data 12 taken from the VL image frames 100.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An imaging system configured to display an image of a tissue onto a display unit, the imaging system comprising:
   a light source for emitting visible light (VL) and near infrared light (NIR);
   a camera head unit configured to capture visible light image data so as to generate a visible light image frame and configured to capture near infrared image data so as to generate an infrared image frame; and
   a camera control unit configured to extract a structural data, the structural data including a texture data, from the visible light image frame and apply the structural data to the infrared image frame so as to enhance the infrared image frame with the structural data, wherein the camera control unit is further configured to convert the visible light image frame into a grayscale image frame prior to extracting the structural data, and is configured to extract the structural data by separating the structural data from the grayscale image frame using an edge-preserving low pass bilateral filter, and wherein the camera control unit is further configured to scale the structural data a predetermined factor so as to generate an enhancement signal, the camera control unit applying the enhancement signal to the near image frame.

2. The imaging system of claim 1, wherein the camera control unit is configured to generate a color map of the near infrared image frame, camera control unit is further configured to apply the structural data to the color map.

3. The imaging system of claim 2, wherein the structural data comprises a texture data.

4. The imaging system of claim 1, wherein the camera control unit is configured to generate an overlaid image frame, the overlaid image frame having the visible light image frame and the color map having the structural data.

5. The imaging system of claim 1, wherein the camera head unit is configured to capture visible light image data so as to generate at least two visible light image frames and is configured to capture near infrared image data so as to generate at least two near infrared image frames, and further wherein the camera control unit is configured to compile the visible light image frames so as to produce a visible light video and compile the near infrared image frames so as to produce a near infrared light video, the camera control unit further configured to apply the structural data to the near infrared image frames so as to enhance the near infrared light video.

6. The imaging system of claim 5, wherein the structural data comprises a texture data.

7. A method for generating a visible light video and a colored light video, the method comprising the steps of:
    obtaining a visible light image frame;
    obtaining an infrared image frame;
    detecting and extracting a structural data, the structural data including a texture data, from the visible light image frame;
    scaling the structural data a predetermined factor;
    applying the structural data to the infrared image frame so as to generate an enhanced infrared image frame;
    converting the visible light image frame into a grayscale image frame prior to extracting the structural data by separating the structural data from the grayscale image frame using an edge-preserving low pass bilateral filter.

8. The method of claim 7, wherein the structural data comprises a texture data.

9. The method of claim 7, further including the step of generating a color map of the infrared image frame, the structural data is applied to the color map, or further including the step of generating an overlaid image frame wherein the color map having the structural data is applied to the visible light image frame.

10. The method of claim 7, wherein the visible light image frame is a plurality of visible light image frames, the plurality of visible light image frames are compiled so as to generate the visible light video and the enhanced infrared image frame is a plurality of enhanced infrared image frames, the plurality of enhanced infrared image frames are compiled so as to generate the colored light video.

* * * * *